United States Patent
Bruchman et al.

Patent Number: 5,584,876
Date of Patent: Dec. 17, 1996

[54] CELL EXCLUDING SHEATH FOR VASCULAR GRAFTS

[75] Inventors: William C. Bruchman; Anita J. Switzer, both of Flagstaff, Ariz.

[73] Assignee: W. L. Gore & Associates, Inc., Newark, Del.

[21] Appl. No.: 235,071

[22] Filed: Apr. 29, 1994

[51] Int. Cl.$^6$ .................................................. A61F 2/06
[52] U.S. Cl. .................................. 623/1; 623/12; 600/36
[58] Field of Search .................................. 623/1, 11, 12; 600/36, 37

[56] References Cited

U.S. PATENT DOCUMENTS

| | | | |
|---|---|---|---|
| 3,626,947 | 12/1971 | Sparks | 623/1 |
| 3,953,566 | 4/1976 | Gore . | |
| 3,974,526 | 8/1976 | Dardik et al. | 623/1 |
| 4,187,390 | 2/1980 | Gore . | |
| 4,321,711 | 3/1982 | Mano | 623/11 |
| 4,482,516 | 11/1984 | Bowman et al. . | |
| 4,816,339 | 3/1989 | Tu et al. | 623/11 |
| 4,911,717 | 3/1990 | Gaskill III | 623/11 |
| 5,084,065 | 1/1992 | Weldon et al. | 600/37 |
| 5,100,422 | 3/1992 | Beguer et al. | 623/1 |
| 5,229,045 | 7/1993 | Soldani | 623/1 |
| 5,348,788 | 9/1994 | White | 623/1 |

FOREIGN PATENT DOCUMENTS

| | | | |
|---|---|---|---|
| 8200091 | 1/1982 | WIPO | 623/1 |
| 8910099 | 11/1989 | WIPO | 623/11 |
| 9324077 | 12/1993 | WIPO | 623/11 |

OTHER PUBLICATIONS

Sauvage et al., "Future Directions in the Development of Arterial Prostheses for Small and Medium Caliber Arteries," *Surgical Clinics of North America* 54:213–228 (1974).

Florian et al., "Small Vessel Replacement With Gore-tex (Expanded Polytetrafluoroethylene)," *Arch. Surg.* 111:267–270 (1976).

Stanley et al., "Biologic and Synthetic Vascular Grafts," *Vascular Surgery, A Comprehensive Review*, Fourth Edition, Chapter 21, pp. 370–389, © 1993.

A. Albini et al., "Fibroblast Chemotaxis," *Collagen Rel. Res.* 5:283–296, (1985).

W. Morzycki et al., "Tumor Necrosis Factor–alpha but not Interleukin–1 Induces Polymorphonuclear Leucocyte Migration Through Fibroblast Layers by a Fibroblast-Dependent Mechanism," *Immunology*, 74:107–113, (1991).

*Primary Examiner*—John G. Weiss
*Assistant Examiner*—Bruce Snow
*Attorney, Agent, or Firm*—Eric J. Sheets; David J. Johns

[57] ABSTRACT

The present invention is directed to a sheath for use with vascular prostheses derived from donor blood vessels, particularly mammalian blood vessels. A vascular prosthesis of the present invention employs an external sheath around a donor blood vessel. The sheath prevents access to the donor vessel wall by host cells originating from perigraft tissue. While resistant to host cell ingrowth, the external sheath is permeable to the flux of macromolecules across its thickness. The exclusion of host cells by the external sheath and the bi-directional flow of macromolecules through the external sheath assists in maintaining the original function of the underlying donor vascular tissue of the prosthesis.

6 Claims, 1 Drawing Sheet

CELL EXCLUDING SHEATH FOR VASCULAR GRAFTS

BACKGROUND OF THE INVENTION

1. Field of the Invention

The present invention relates to vascular prostheses improved through the use of an external sheath that is resistant to cell ingrowth while being permeable to flux of fluid and macromolecules across the thickness of the sheath. The sheath can also impart mechanical strength to the vascular tissue of the prostheses.

2. Description of Related Art

Blood vessels taken from human or animal donors have been widely used to replace blocked, aneurysmal, or otherwise damaged arteries and veins. Both living and preserved human arterial allografts were extensively used as arterial substitutes in the 1950's and this initial use appeared successful. However, human allografts were largely abandoned by 1960 due to a high incidence of thrombosis, stenosis, and aneurysmal dilatation.

The practice of grafting with allogeneic arteries was abandoned in favor of the mechanically superior alternative of using vascular grafts made of synthetic materials. The synthetic materials principally used for this grafting are polyethylene terephthalate and expanded polytetrafluoroethylene (ePTFE). These materials offer biocompatibility and provide sufficient mechanical integrity to prevent aneurysmal dilation. Prosthetics made of these materials were shown to be successful in the replacement of large vessels such as the aorta or iliac arteries and are still successfully used in these applications. Although successful when used in large diameter applications, the patency performance of these materials in demanding small diameter applications such as coronary artery bypass or peripheral arterial bypass distal to the popliteal artery, for example, has been substantially less than that of transplanted living autologous vessels.

Regardless of whether a prosthetic vascular graft is obtained from a donor or is made of synthetic materials, it has been a common belief since the 1950's that ingrowth of host tissue into vascular grafts leads to improved function. Representative of this belief is the following statement: "With existing prostheses, we believe that the best assurance of long term patency without complication is attainment of complete healing of the prosthetic wall, which includes an endothelialized flow surface. This final healed state is principally dependent upon the ingrowth of areolar tissue from perigraft sources through the interstices of a pervious graft wall." (Sauvage et al., "Future Directions in the Development of Arterial Prostheses for Small and Medium Caliber Arteries," *Surgical Clinics of North America* 54:213–228 (1974))

With biologically-derived prosthetics, host tissue ingrowth is observed to alter the donor graft material into one composed at least partially of recipient tissues. In addition, such ingrowth of autologous tissues usually generates a blood interface in the prosthetic replacement composed in part of tissues of the host.

In the case of porous synthetic materials, autologous tissue ingrowth occurs through the interstices of the material. The apparent desirability of ingrowth of autologous tissue into grafts made of porous polytetrafluoroethylene (ePTFE) is illustrated by the results of a study comparing the patency performance of small caliber vascular ePTFE prosthetics having different porosities. The study showed that high porosity ePTFE grafts with a fibril length of 100 µm had pronounced ingrowth of fibrous tissue into the interstices of the graft and remained 100% patent at six months postoperatively. Low porosity ePTFE grafts with a short fibril length (10) had layers of tissue on either side of the graft wall, but no ingrowth of tissue into the interstices of the graft. These low porosity grafts were 67% patent at six months postoperatively. (Florian et al., "Small Vessel Replacement With Gore-tex (Expanded Polytetrafluoroethylene)," *Arch. Surg.* 111:267–270 (1976))

The initial theory concerning performance of vascular grafts was proposed by Wesolowski in 1963. This theory, based upon the conclusion that ingrowth of host cells leads to better patency performance, remains the predominate theory today. (See for example, Stanley et al., "Biologic and Synthetic Vascular Grafts," *Vascular Surgery, A Comprehensive Review*, Fourth Edition, Chapter 21, pp 370–389, ©1993, referring to Wesolowski, S. A., Dennis, C., "Fundamentals of Vascular Grafting," New York, McGraw-Hill, 1963)

Intentional exclusion of host cells from the interstices and lumen of a vascular graft in order to prevent the host cells from adversely affecting the patency performance of the vascular graft has not been previously described. Moreover, application of an external porous synthetic sheathing material to a vascular graft that prevents disruption or remodeling of the graff by host cells while being permeable to the flux of biological fluids and molecules across its thickness has heretofore not been described.

SUMMARY OF THE INVENTION

The present invention is directed to improved vascular prostheses derived from donor blood vessels. It is an object of the present invention to provide improved performance for vascular prostheses by preventing many of the failures that are a consequence of the invasion of an implant by host cells. It is a further object of the present invention to provide improved performance for vascular prostheses by providing a cell excluding covering for the vascular tissue of a prosthesis that permits exchange of biological fluids and substances across the vascular tissue of the implant and the perigraft tissue of a recipient.

Contrary to the widely accepted theory that the performance of vascular grafts is enhanced by host tissue ingrowth, the present invention achieves enhanced patency performance of vascular grafts by employing an external sheath around a donor blood vessel that is resistant to host cell ingrowth originating from perigraft tissue.

It has been discovered that ingrowth of host cells into a vascular graft derived from donor blood vessels often causes disruption of the function of the graft. Such remodeling can have serious negative consequences, such as mechanical failures in the form of aneurysmal dilatation, anastomotic dehiscence, frank graft disruption, as well as thrombosis related to the alteration of the blood vessel wall composition. By blocking the access of host cells to the donor blood vessel with a cell excluding sheath of the present invention, the host cells responsible for remodeling the vessel walls cannot grow into the donor blood vessel and disrupt the architecture of the vessel walls. As a result, many of the above-mentioned vascular graft failures can be delayed or prevented.

It has also been discovered that permeability of the cell-excluding external sheath of the present invention to ions, water, and macromolecules, for example, is necessary for maintaining the function of the donor blood vessel after implantation. Permeability of the external sheath is achieved by constructing the sheath so that it is microporous.

Accordingly, the present invention is a covering for a blood vessel which comprises a sheath surrounding the blood vessel, wherein the sheath comprises a microporous polymeric material and wherein the sheath serves as a barrier to external cellular contact to the blood vessel, while being permeable to macromolecules.

DESCRIPTION OF THE DRAWINGS

The operation of the present invention should become apparent from the following description when considered in conjunction with the accompanying drawings, in which.

DETAILED DESCRIPTION OF THE INVENTION

The present invention is directed to a sheath for use in vascular prostheses derived from donor blood vessels, particularly mammalian blood vessels. A vascular prosthesis may employ an external sheath of the present invention around a donor blood vessel. The sheath prevents access to the donor vessel wall by host cells originating from perigraft tissue. While resisting host cell ingrowth, the external sheath is permeable to the flux of macromolecules across its thickness. The exclusion of host cells by the external sheath and the bi-directional flow of macromolecules through the external sheath assists in maintaining the original function of the underlying donor vascular tissue of the prosthesis. The term "macromolecules" is understood to include, but not be limited to, molecules having a molecular weight up to and including about 2,000,000 MW.

In the present invention, it has been found that the original architecture and function of vessel derived vascular grafts can be maintained if invasion of the donor vessel wall by host cells is prevented while the flux of macromolecules across the wall is permitted. If the original architecture and function of the arterial wall of a vascular graft is so maintained, many of the failures previously noted with transplanted vessels can be prevented, resulting in improved patency performance of these biologically derived grafts. The teachings of the present invention are thus directly opposite those of the prior art in this field regarding the desirability of host cell ingrowth into the donor tissue of a biological vascular graft.

Figure 1:
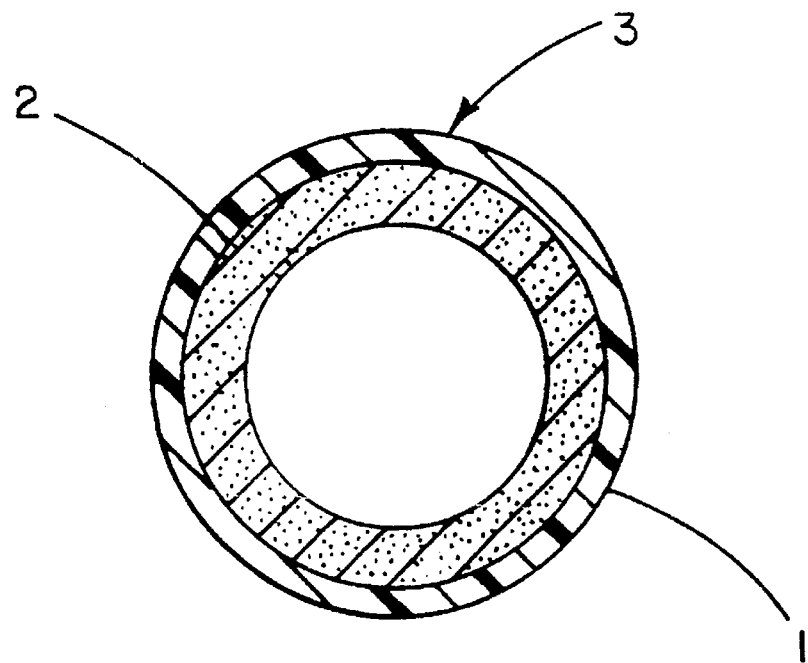
FIG. 1 is a cross-sectional view of a mammalian artery having the external sheath applied.
Figure 2:
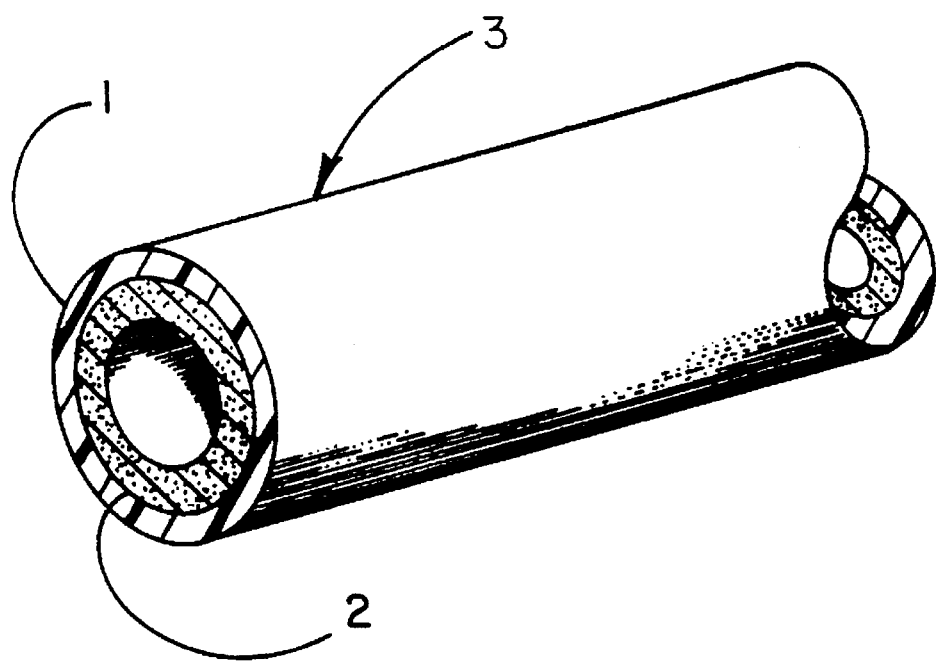
FIG. 2 is another view of the embodiment of the present invention illustrated in FIG. 1.

Since host cellular invasion largely proceeds from the perigraft region radially toward the lumen, prevention of cellular invasion of the donor blood vessel wall used as a vascular graft is achieved by application to the external surface of the vessel wall of a sheath that is resistant to cell ingrowth. A structure resembling this configuration is shown in FIGS. 1 and 2. The sheath 1 is applied to the external surface of a mammalian blood vessel 2 forming a tubular vascular graft 3. The flux of macromolecules across the thickness of the external sheath is achieved by constructing the sheath of materials that are permeable to macromolecules while being resistant to cell ingrowth. The preferred materials for construction of the external sheath are synthetic materials that are microporous. Suitable materials for construction of the external sheath of the present invention include, but are not limited to, the group of polymer materials with demonstrated biocompatibility and stability under implant conditions, such as, polytetrafluoroethylene (PTFE), polyethylene terepthalate, fluorinated ethylene propylene (FEP), polyethylene, polypropylene, and siloxane, for example. The external sheath employed in the preferred embodiment of the present invention is made of expanded PTFE (ePTFE) as produced in U.S. Pat. No. 3,953,566, issued to Gore, which is incorporated herein by reference.

The pore size that is effective in resisting cell ingrowth across the thickness of the sheath is dependent upon the thickness of the wall itself and the tortuosity of the pores connecting the outer surface with the inner surface of the sheath. In the case of regular uniform pores in a thin sheath construction (about 10–20 µm in thickness) the pores should be selected to be less than about 3 µm. This value is based upon Boyden chamber migration assays where the limit of fibroblast invasion of straight, uniform pores is about 5–8 µm and the limit of leukocyte invasion through straight, uniform pores is about 3–5 µm. (A. Albini et al., "Fibroblast Chemotaxis," *Collagen Rel. Res.* 5:283–296, (1985); W. Morzycki et al., "Tumor Necrosis Factor-alpha but not Interleukin-1 Induces Polymorphonuclear Leucocyte Migration Through Fibroblast Layers by a Fibroblast-Dependent Mechanism," *Immunology,* 74:107–113, (1991)) In the case of a thicker, more tortuous, or laminate structure, the individual pores can be somewhat larger and still serve as an effective barrier to the passage of cells across the layer.

For an ePTFE or similar fibrillated sheath, the pore size of the sheath is related to the fibril length of the sheath material and the thickness of the sheath material. Thicker fibrillated sheath materials generally have more tortuous pathways connecting one end of a pore to the other end of the pore. As a result, a thicker fibrillated sheath may have pores that are larger than invading cells, but will remain resistant to cell ingrowth due to the increased tortuosity of the pathways of the pores in thicker sheath material. Regardless of the thickness of the sheath, the fibril length should be chosen to form pores that resists cellular access through the sheath, while being permeable to macromolecules.

In defining the ability of the sheath to resist cell ingrowth, a noncellular assay method has been developed. Based upon the published values that 3 µm represents the lower limit of cell permeability through straight pores, 3 µm microspheres can be used to mechanically determine whether a given sheath will exclude particles of this diameter. Consequently, any sheath material that excludes 3 µm microspheres should effectively prevent cellular movement across the sheath.

Fibril length is measured as described in U.S. Pat. No. 4,482,516, issued to Boman et al, which is incorporated herein by reference. The fibril length of porous ePTFE that has been expanded in a single direction is defined herein as the average of ten measurements between nodes connected by fibrils in the direction of expansion. Ten measurements are made in the following manner. First, a photomicrograph is made of a representative portion of the sample surface, of adequate magnification to show at least five sequential fibrils within the length of the photomicrograph. Two parallel lines are drawn across the length of the photomicrograph so as to divide the photograph into three equal areas, with the lines being drawn in the direction of expansion and parallel to the direction of orientation of the fibrils. Measuring from left to right, five measurements of fibril length are made along the top line in the photograph beginning with the first node to intersect the line near the left edge of the photograph and continuing with consecutive nodes intersecting the line. Five more measurements are made along the other line from fight to left beginning with the first node to intersect the line on the right hand side of the photograph. The ten measurements obtained by this method are averaged to obtain the fibril length of the material.

For a porous, ePTFE material that has been expanded in more than one direction, the fibril length is estimated by examining a representative photomicrograph of the material surface and comparing fibril lengths as described above in a manner that represents the various directional orientations of the fibrils.

The sheath may be constructed in a tubular configuration and applied to the external surface of a stabilized artery. An external sheath can also be applied as a film to the outside of a donor blood vessel, and the film layers subsequently bonded together.

Once a pore size and construction method are chosen for the sheath, the permeability characteristics of the sheath can be evaluated by testing with markers of known size, such as dextrans and polystyrene microspheres. For example, dextran, with an average molecular weight of about 2,000,000 MW, labelled with the colored compound fluorescein (Sigma Chemical Co., St. Louis, Mo.), can be used to test the ability of the sheath to pass macromolecules. Cell impermeability of the sheath can be tested using polystyrene microspheres with a diameter of about 3 μm (Polysciences, Inc., Warrington, Pa.) at a concentration of about 2.5% solids in suspension, for example.

When testing the sheath for permeability with colored markers, the markers are suspended as an aqueous solution or as an aqueous suspension at concentrations sufficient to provide a distinctly visible color. The preferred concentration of the fluorescein-labeled dextran solution is approximately 0.2 mg dextran/ml. The preferred concentration of the suspension of the polystyrene microspheres is approximately 0.02 ml microspheres/ml suspension, to yield about $4.5 \times 10^7$ beads/ml suspension. The evaluation of the sheath permeability occurs at about 23° C. The sheath is prepared for permeability testing by rendering it permeable to water, if necessary. For example, sheaths constructed of ePTFE are wetted with 100% ethyl alcohol and then flushed with water to remove the alcohol before permeability testing.

To test the permeability of the sheath to macromolecules, the dextran test solution is instilled in the lumen of a sheath and pressurized to about 20.7 kPa using a syringe. The contents of the syringe are forced through the sheath and the liquid that filters through the sheath wall is collected and visually inspected against a white background for evidence of the colored dextran.

In preparation for testing the permeability of a sheath to cells, the number of microspheres in the suspension are determined by using an appropriate counting device, such as a hemacytometer, for example. The permeability of the sheath is then tested by forcing the microsphere-containing suspension through the sheath material at about 20.7 kPa using a syringe. The syringe is refilled with water and the water also forced through the sheath at about 20.7 kPa. The liquid that filters through the sheath wall is collected and subjected to centrifugation at about 300×g for about 5–10 minutes. The supernatant is decanted and discarded and the pellet of microspheres is resuspended in a known volume of water. The number of microspheres in the resuspended pellet are counted and compared with the original suspension. The number of microspheres that pass through the sheath are expressed as a percentage of the number introduced into the lumen of the sheath. An appropriate sheath for use in the present invention will pass the about 2,000,000 MW dextran at pressures at or below about 20.7 kPa so that the colored solution that filters through the sheath is clearly visible when viewed against a white background. Additionally, the sheath will not allow more than about 5% of the 3 μm microspheres to pass across its thickness at a pressure of about 20.7 kPa.

Some suitable methods for applying the sheath of the present invention to vascular prostheses derived from naturally occurring tissue and vascular prostheses using synthetic materials are included a in U.S. patent application of Bruchman et al., entitled "Improved Blood Contact Surfaces Employing Natural Subendothelial Matrix And Method Of Making And Using Same," which is simultaneously filed herewith and incorporated herein by reference. It is understood that the vascular tissue preparation processes described in simultaneously filed application are only some of the suggested uses of the sheath of the present invention.

In addition to preventing ingrowth of host cells into the prosthesis of the present invention, while being permeable to macromolecules, the sheath of the present invention can also function as a component of a vascular prosthesis that supplies mechanical reinforcement for the prosthesis. While a biologic component of the graft, such as a donor blood vessel, supplies the antithrombotic properties to the vascular prosthesis, the long term mechanical stability is usually supplied by the sheath component. Accordingly, the sheath of the present invention is selected to provide mechanical strength necessary for the particular diameter of the graft used in order to resist the hoop stress induced by blood pressure, and to provide sufficient mechanical strength to resist anastomotic stresses.

The sheath is constructed by wrapping a mandrel with multiple layers of ePTFE film, such as those described in U.S. Pat. Nos. 3,953,566 and 4,187,390 both issued to Gore, each of which is incorporated herein by reference, and adhering the film to itself by heating the film and mandrel in an oven at about 380° C. for about 10 to about 20 minutes. The film tube is removed from the mandrel and prepared tissue graft installed in the lumen of the polymeric tube. Other materials, or combinations of materials, may be applied to the tissue tube similarly, using temperatures and times appropriate for the physical properties of the chosen material.

Other methods of manufacturing the sheath material include placing a processed artery onto a mandrel and wrapping the artery with multiple layers of an ePTFE and FEP composite film, and heating the film layer very briefly from about 325° C. to about 350° C. to adhere the film wrap to itself on the outer surface of the vessel. The FEP-coated ePTFE film is made by a process which includes the steps of: a) contacting a porous PTFE substrate, usually in the form of a membrane or film, with another layer which is preferably a film of FEP or alternatively of another thermoplastic polymer; b) heating the composition obtained in step (a) to a temperature above the melting point of the thermoplastic polymer; c) stretching the heated composition of step (b) while maintaining the temperature above the melting point of the thermoplastic polymer; and d) cooling the product of step (c).

Another sheath construction method is the fabrication of a tubular form of ePTFE constructed according to U.S. Pat. No. 3,593,566 to Gore using a uniaxial expansion. The processed blood vessel is inserted into the ePTFE tube so constructed. As in the other forms of the sheath, the tubular form must be permeable to the passage of macromolecules but exclude the passage of cells.

Structures of Sheaths Made in Accordance with the Present Invention

Without intending to limit the scope of the present invention, the following examples illustrate how the present invention can be made and used.

EXAMPLES

Example 1

Film Sheath Construction

A sheath tube was constructed from a porous expanded polytetrafluoroethylene (ePTFE) film. The porous ePTFE film from which the sheath tube of the present invention was constructed, was made as taught by U.S. Pat. No. 3,953,566, issued to Gore, and U.S. Pat. No. 4,187,390, issued to Bowman et al each of which is incorporated herein by reference.

This porous ePTFE film had a microstructure of nodes interconnected by fibrils. The films was made by expansion by stretching in a single direction, which was the direction in which the resulting fibrils were primarily oriented. The film used in the preparation of this invention had a fibril length of about 50 µm, a density of about 0.3 g/cm, a thickness of about 0.01 mm, and were 86% porous by bulk volume. The fibril length of the porous ePTFE film referred to above was an estimated mean value obtained by examining a scanning electron photomicrograph of the film.

To construct the sheath, the film was applied to a metal mandrel about 5 mm in diameter by wrapping the mandrel with the film in a helical manner. The pitch of the helix was such that each wrap of film overlapped approximately two-thirds of the previous wrap. The mandrel was wrapped three times in this fashion, resulting in a film tube constructed of about nine layers of film. The wrapped mandrel was then heated in a oven at about 378° C. for seven minutes to adhere the film layers together. The mandrel was removed from the oven and allowed to cool. Once cool, the film sheath was removed from the mandrel.

The sheath was tested for ability to pass macromolecules as follows. A solution of fluorescein-labeled dextran with an average molecular weight of 2,000,000 MW was prepared in water at a concentration of about 0.2 mg/ml. A portion of the sheath, about 10 cm in length, was mounted on a barbed Luer fitting and wetted with 100% ethyl alcohol. The alcohol was removed by flushing the sheath with water using a syringe to force the water through the pores of the sheath. Using a syringe, the dextran test solution was instilled in the lumen of the sheath and pressurized to about 20.7 kPa. The contents of the syringe were forced through the sheath and the liquid that filtered through the sheath wall was collected and visually inspected against a white background for evidence of the colored dextran. The solution was distinctly yellow colored, and the sheath, therefore, permeable to macromolecules.

The sheath was tested for ability to prevent cellular infiltration. A second 10 cm length of sheath was wetted with ethyl alcohol and the alcohol replaced with water as described above. The number of microspheres in the suspension was determined to be about $4.7 \times 10^7$ spheres/ml using a hemacytometer. The microsphere-containing suspension was tested by forcing the contents of the syringe, 5 ml of stock suspension, through the sheath material at 20.7 kPa. The syringe was refilled with water and the water also forced through the sheath at 20.7 kPa. The liquid that filtered through the sheath wall was collected and subjected to centrifugation at about 300×g for 5 minutes. The supernatant was decanted and discarded, and the pellet of microspheres was resuspended in one ml of water. The number of microspheres in the resuspended pellet was counted as for the original suspension and the count expressed as a percentage of the number of microspheres used for the test. The percentage of microspheres passing through the wall of the sheath was 0.17%. The sheath can be considered resistant to cell ingrowth since less than 5% of the microspheres pass through the sheath wall.

A sheath of porous ePTFE was constructed. The sheath was permeable to macromolecules and resistant to cellular infiltration by the defining tests. The sheath can be installed onto arterial replacement grafts comprised of tissue from allogeneic or xenogeneic sources by sliding the processed artery into the lumen of the sheath.

Example 2

Enzyme Milling

Carotid arteries removed from a donor dog were placed in 15% dimethylsulfoxide in Hanks' Balanced Salt Solution (DMSO/HBSS) and stored in liquid nitrogen. For treatment, the arteries were thawed, rinsed in HBSS, and the adventilia dissected from the arteries. Both arteries were mounted onto barbed Luer fittings.

Both arteries were filled with calcium and magnesium free HBSS containing 0.4 mM ethylenediamine tetraacetic acid (EDTA) to inhibit the action of collagenase that may penetrate to the lumen. The ends of the arteries were plugged and the arteries rinsed again in HBSS. Both arteries were immersed in separate incubation tubes containing 0.2M Tris-HCl, pH 7.5, containing 0.1M ε-amino-n-caproic acid, 5 mM N-ethylmaleimide, 5 mM benzamidine, and 0.36 mM $CaCl_2.2H_2O$ (all from Sigma Chemical Co., St. Louis, Mo.). To one tube, 35 units of type 1A collagenase (Sigma) per ml of buffer was added. Both arteries were incubated at 37° C. for about 5.5 hours.

After incubation, the arteries were rinsed thoroughly in HBSS and were sleeved with a 5 mm tube and pressure fixed in 0.25% glutaraldehyde in 0.020M N-2-hydroxyethylpiperazine-N'-2-ethane sulfonic acid (HEPES), pH 7.3, with 0.44% NaCl and 0.26% $MgCl_2.6H_2O$, at about 27.6 kPa for about 2 hours. The arteries were then removed from their sleeves and left immersed in the fixing solution overnight. After fixing, the arteries were rinsed thoroughly in normal saline and sleeved with the sheath from Example 1. The finished wall thickness of the sleeved digested artery was 0.14 mm while the finished wall thickness of the sleeved control artery was 0.22 mm.

Example 3

Sheath Applied Directly to Fixed Artery

Distal limbs were obtained from cows at slaughter and stored frozen at about −20° C. until required for processing. The legs were thawed by immersing them in warm (37° C.) water and the arteries dissected from the legs. After rinsing in Hanks' Balanced Salt Solution (HBSS), the adventitia was dissected free and the arteries stored in HBSS until fixed.

Arteries of an appropriate size to provide a finished internal diameter of approximately 4 mm were selected. The arteries were sleeved with 5 mm GORE-TEX® Vascular Graft (W. L. Gore & Associates, Inc., Flagstaff, Ariz.), mounted on barbed Luer fittings and were pressure fixed at about 27.6 kPa for 2 hours in 2.5% glutaraldehyde in 0.2M Sorenson's phosphate buffer, pH 7.0. Fixation occurred at about 23° C. After fixation, the arteries were rinsed in normal saline, and stored in normal saline at about 4° C. until required for use.

Application of the sheath to the fixed arteries was performed as follows. The artery was placed onto a 3 mm diameter mandrel and the ends of the artery secured with wire ties. Next, a helical wrap of 25.4 mm wide film was applied over the outer surface of the arteries. The film used for the helical wrapping was a porous ePTFE film with an additional layer or coating of fluorinated ethylene propylene (FEP) on one surface. The FEP-coated porous ePTFE film was made by a process which comprises the steps of:

a) contacting a porous ePTFE substrate, usually in the form of a membrane or film, with another layer which is preferably a film of FEP or alternatively of another thermoplastic polymer;

b) heating the composition obtained in step (a) to a temperature above the melting point of the thermoplastic polymer;

c) stretching the heated composition of step (b) while maintaining the temperature above the melting point of the thermoplastic polymer; and d) cooling the product of step (c).

The FEP coating of the porous ePTFE film for this example was discontinuous, thereby resulting in a porous composite film. The porous FEP-coated ePTFE film used to make this example had a thickness of about 0.03 mm, a density of about 0.3 g/cc, a fibril length of about 40 µm, and a width of about 25.4 mm.

The FEP-coated side of the film was placed against the fixed arterial tissue. The pitch of the helical wrap was chosen such that each wrap of the film overlapped approximately two-thirds of the prior wrap. The arteries were wrapped three times in this fashion, resulting in a film layer constructed from about nine layers of film. While still on the mandrel, the film-wrapped arteries were contacted very briefly by an aluminum fixture heated to about 350° C. to thermally bond the layers of film together while minimizing the heating of the fixed artery. The fixture was an aluminum ring with an internal diameter of about 0.8 cm, a wall thickness of about 1.5 cm and an overall length of about 5 cm. The process employed to bond the film layers was to place the wrapped artery through the hole in the fixture, contact the surface of the film to the heated fixture and rotate the graft assembly. One revolution of a graft with an outside diameter of about 5 mm was performed in 1.5 to 2.0 seconds. After heating, the wire ties attaching the artery to the mandrel were removed and the fixed artery with the sheath applied removed from the mandrel.

The artery-sheath composite was stored in normal saline or water until permeability testing of the sheath could be performed. The sheath was removed from the artery and the artery discarded. The sheath was tested for ability to pass macromolecules and to prevent cellular infiltration as described in Example 1. The sheath, when pretreated by wetted with 100% ethyl alcohol, readily passed the 2,000,000 MW dextran, indicating that a sheath constructed in this fashion was permeable to macromolecules. The same sheath allowed no measurable quantity of the 3 µm microspheres to pass through, indicating that this sheath construction is resistant to cellular infiltration.

Example 4

Burst Testing of Sleeved and Unsleeved Fixed Arterial Tissue

Carotid arteries from a greyhound dog were placed into normal saline. The adventitia was dissected away and the arteries were mounted on barbed Luer fittings and sleeved with a 5 mm GORE-TEX® Vascular Graft (W. L. Gore & Associates, Inc., Flagstaff, Ariz.) to provide a fixed artery with about a 4 mm internal diameter. The arteries were pressure fixed at about 27.6 kPa for two hours at 23° C. in 2.5% glutaraldehyde in 0.2M Sorenson's phosphate buffer, pH 7.0. After fixation, the fixing sleeves were removed and the arteries rinsed in normal saline overnight.

One artery of the pair was sleeved with the sheath described in Example 1. The other was unsleeved. Testing occurred at about 23° C. To test, each artery was slipped over a segment of latex tubing and one end of the tubing and graft assembly connected to a pressure source. The tubing was filled with water and the other end of the assembly clamped with a hemostat. The water pressure inside the tubing was increased at about 69 kPa/sec until the graft raptured. The pressure at which rupture occurred was recorded.

The fixed artery segment with no sheath applied ruptured at about 579 kPa. The fixed artery segment with the sheath material applied ruptured at about 1358 kPa, demonstrating that the sheath material provides an improvement in strength to the fixed artery.

Example 5

Permeable and Impermeable Sheath Constructions

Permeability of the sheath of the present invention to macromolecules, while being resistant to host cell ingrowth is a necessary element in providing improved patency performance of donor blood vessels. In this example, permeable and impermeable sheaths were constructed from GORE-TEX® ePTFE tubing prepared as described in U.S. Pat. No. 3,953,566, issued to Gore, which is incorporated herein by reference. The tubing had a mean fibril length of 5 µm, an internal diameter of about 5 mm, and a wall thickness of about 0.48 mm.

The tubing was cut into segments about 10 cm in length. Half of the segments were rendered impermeable by wetting the tubing with 1,1,2 trichloro-1,2,2-trifluoroethane (Freon TF, E. I. dupont de Nemours, Inc., Wilmington, Del.) and infiltrating the pores of the tubing with a 50% (approximate) (v:v) mixture of 1,1,2 trichloro-1,2,2-trifluoroethane and Silastic Type A Medical Grade Adhesive (Dow Corning, Inc., Midland, Mich.). The tubing was then placed on a 5 mm diameter mandrel and additional unthinned adhesive was applied to the outer surface of the tubing. The tubing was placed in a forced air oven at about 100° C. for approximately two hours to cure the adhesive. Both the impermeable tubing and a section of untreated GORE-TEX® ePTFE tubing were cut to 5 cm and sterilized by autoclave.

The permeable and impermeable sheaths described above were tested for the capacity to pass macromolecules but block the passage of cells using the procedure described in Example 1. The impermeable silicone-coated sheath blocked the passage of the 2,000,000 MW dextrans and the 3 µm beads. The uncoated permeable sheath passed the dextran molecules, but did not allow the 3 µm beads to pass. Thus, the above constructions provided a sheath that is impermeable to macromolecules and cells, and a sheath that is permeable according to the requirements of the present invention.

The arterial tissue to be sleeved with the sheaths prepared above was obtained from the femoral arteries of a greyhound dog. A 6 cm length of both femoral arteries was removed and the arterial branches ligated with silk ligatures. Each artery was placed in 15% DMSO in HBSS and frozen in liquid nitrogen for 15 days.

The arteries were prepared for implantation into a recipient greyhound dog by first thawing the frozen arteries. The arteries were rapidly thawed by immersing the freezing tubes containing the arteries in 37° C. water. The arteries were rinsed in saline and the adventitia trimmed. One end of each artery was attached to a barbed Luer fitting and the arteries sleeved with a segment of 5 mm GORE-TEX® Vascular Graft (W. L. Gore & Associates, Inc., Flagstaff, Ariz.) so that when fixed in glutaraldehyde, the arteries would have a finished internal diameter of about 4 mm and an outer diameter of 5 mm. The arteries were pressure fixed in 2.5% glutaraldehyde (v:v) in 0.2M Sorenson's phosphate buffer, pH 7.0 at about 27.6 kPa for 2 hours.

Using sterile technique, the arteries were removed from the glutaraldehyde solution, cut free of the fittings, and the GORE-TEX® graft sleeves removed. The arteries were immersed in 500 ml of sterile normal saline to remove the excess glutaraldehyde, and stirred at room temperature for 15 minutes, at which time the saline was replaced with 500 ml of fresh sterile normal saline. The arteries were rinsed for an additional 15 minutes in the fresh sterile saline. At the end of the second rinse, the arteries were stored in fresh sterile normal saline until required for implantation.

For implantation, each fixed artery segment was placed within the lumen of one of the sterile sheaths previously prepared. The ends of the fixed arteries were cut flush with the ends of the sheaths. The composite grafts so constructed were about 5 cm in length.

The femoral arteries of a recipient greyhound dog were surgically exposed and a segment of about 5 cm excised from both femoral arteries. Each graft was surgically interposed into one of the femoral arteries using end-to-end technique and a continuous suture. Both layers of the composite grafts were anastomosed to the host femoral arteries with CV-6 GORE-TEX® suture (W. L. Gore & Associates, Inc., Flagstaff, Ariz.).

At 19 days following implantation, the femoral artery replaced with a processed artery covered with the impermeable sheath was found to be occluded by duplex scanner ultrasonography. Occlusion was confirmed at 20 days postoperation with contrast arteriography.

After 60 days implantation, the remaining femoral artery replaced with a processed artery covered with a permeable sheath of the present invention was visualized using arteriography and was found to be patent.

Thus, the fixed graft with the impermeable sheath was found occluded at 19 days after implantation, while the graft with the selectively permeable sheath of the present invention remained patent for at least 60 days, at which time the grafts were explanted and the patent graft subjected to histological studies. Histological examination of the patent graft showed the inner layers of the biologic component of the patent graft had maintained the architecture of the original donor artery.

These results demonstrate that the use of the sheath of the present invention with a preserved donor artery in a vascular prosthesis provides improved patency performance compared to a preserved donor artery having an impermeable sheath.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A vascular graft in the form of a covered blood vessel which comprises:

a sheath surrounding a blood vessel derived from a donor; wherein the sheath comprises a microporous material; and wherein the sheath serves as a barrier to external cellular ingrowth into the blood vessel, while being permeable to macromolecules.

2. The covered blood vessel of claim 1 wherein the sheath permits the flow of macromolecules therethrough up to a molecular weight of approximately 2,000,000 MW.

3. The covered blood vessel of claim 1 wherein the microporous polymeric material is selected from the group consisting of at least one of polytetrafluoroethylene, polyethylene terepthalate, fluorinated ethylene propylene, polyethylene, polypropylene, and siloxane.

4. The covered blood vessel of claim 1 wherein the sheath comprises an expanded polytetrafluoroethylene.

5. A vascular graft in the form of a covered blood vessel which comprises:

a blood vessel derived from a donor;

a sheath of microporous polymeric material, the microporous polymeric material excludes cell ingrowth and cell passage therethrough;

wherein the sheath contains the donar blood vessel to reinforce the blood vessel and to protect the blood vessel along its length from ingrowth of host cells, while allowing the passage of water and macromolecules through the sheath.

6. A method for producing a vascular graft which comprises:

providing a blood vessel derived from a donor, providing a sheath comprising a microporous polymeric material comprised of expanded polytetrafluoroethylene that excludes cell passage therethrough, while allowing the flow of water and macromolecules through the sheath;

covering the blood vessel with the sheath so as to reinforce the blood vessel and to protect the blood vessel along its length from ingrowth of host cells, while allowing the flow of water and macromolecules through the sheath.

* * * * *